(12) United States Patent
Zhang et al.

(10) Patent No.: US 8,778,653 B2
(45) Date of Patent: Jul. 15, 2014

(54) METHOD FOR REDUCING DNA IMPURITIES IN VIRAL COMPOSITIONS

(75) Inventors: Yi Zhang, Beijing (CN); Jinming Dai, Beijing (CN); Yajin Ni, Gaithersburg, MD (US)

(73) Assignee: Yisheng Biopharma Holdings Ltd., Kaifeng (CN)

( * ) Notice: Subject to any disclaimer, the term of this patent is extended or adjusted under 35 U.S.C. 154(b) by 20 days.

(21) Appl. No.: 13/813,897

(22) PCT Filed: Aug. 12, 2010

(86) PCT No.: PCT/CN2010/075948
§ 371 (c)(1),
(2), (4) Date: Apr. 11, 2013

(87) PCT Pub. No.: WO2012/019354
PCT Pub. Date: Feb. 16, 2012

(65) Prior Publication Data
US 2013/0203152 A1  Aug. 8, 2013

(51) Int. Cl.
*C12N 7/02* (2006.01)
*C12N 7/06* (2006.01)
*A61K 39/12* (2006.01)
*C12N 7/00* (2006.01)
*A61K 39/00* (2006.01)

(52) U.S. Cl.
CPC . *C12N 7/02* (2013.01); *A61K 39/12* (2013.01); *C12N 2760/20134* (2013.01); *C12N 7/06* (2013.01); *C12N 7/00* (2013.01); *A61K 2039/525* (2013.01); *C12N 2760/20151* (2013.01)
USPC .............................. 435/239; 435/238; 530/417

(58) Field of Classification Search
CPC .............. C12N 7/02; C12N 7/04; C12N 7/06; C12N 2760/20151; A61K 39/205; A61K 2039/525; A61K 2039/5252
See application file for complete search history.

(56) References Cited

U.S. PATENT DOCUMENTS

2007/0207461 A1* 9/2007 Weggeman et al. .............. 435/6

FOREIGN PATENT DOCUMENTS

| CN | 1712068 | 12/2005 |
|----|---------|---------|
| CN | 1966076 | 5/2007 |
| CN | 101352570 | 1/2009 |
| CN | 101695570 | 4/2010 |
| WO | WO2006108707 | 10/2006 |
| WO | WO2007123961 | 11/2007 |
| WO | WO2008006780 | 1/2008 |

OTHER PUBLICATIONS

Kalbfuss et al. Purification of Cell Culture-Derived Human Influenza A Virus by Size-Exclusion and Anion-Exchange Chromatography. Biotechnology and Bioengineering 2007, vol. 96, No. 5, pp. 932-944.*
Transfiguracion et al. Size-Exclusion Chromatography Purification of High-Titer Vesicular Stomatitis Virus G Glycoprotein-Pseudotyped Retrovectors for Cell and Gene Therapy Applications. Human Gene Therapy, Aug. 2003, vol. 14, pp. 1139-1153.*
Kumar et al. Process Standardization for Optimal Virus Recovery and Removal of Substrate DNA and Bovine Serum Proteins in Vero Cell-Derived Rabies Vaccine. Journal of Bioscience and Bioengineering 2002, vol. 94, No. 5, pp. 375-383.*
International Search Report (Form PCT/ISA/210) for PCT/CN2010/075948, mailed on May 26, 2011, 4 pages.
Supplementary European Search Report for European application No. EP 10 85 5775, mailed on Jan. 17, 2014, 2 pages.
Lu, et al., "The selection of the purified methods to the purified Vero cell rabies vaccine 1-8 for human", Progress in microbiology and Immunology,1005-5673, vol. 28., No. 4, 2000. Abstract Only.
Li, et al., "Li Fu-an et al, The influence of sample concentration upon the purification effect of rabies vaccine (Vero cell culture) during process of gel column chromatography", Progress in microbiology and Immunology, 1005-5673, vol. 30, No. 3., 2002. Abstract Only.
Lu, et al., "On the Study Purification of the Rabies Vaccine Developed From Hamster Kidney Cells", Chinese Journal of Zoonoses, 1002-2694, vol. 15., No. 2., 1999. Abstract Only.
Kumar, et al., "Purification, potency and immunogenicity analysis of Vero cell culture-derived rabies vaccine: a comparative study of single-step column chromatography and zonal centrifuge purification", Microbes Infect. 2005, 7 (9-10):1110-6.

* cited by examiner

*Primary Examiner* — Louise Humphrey
(74) *Attorney, Agent, or Firm* — Shweta Chandra; Elizabeth A. Alcamo; Bozicevic, Field & Francis, LLP

(57) ABSTRACT

A method for purification of viral compositions is provided. In particular, a method for reduction of unwanted residual DNA in a viral composition while retaining the immunogenicity of the virus itself is provided. The resulting immunogenic viral composition is substantially free of residual DNA, and is useful for the manufacture of medical products, such as vaccines designed for human or animal.

7 Claims, No Drawings

METHOD FOR REDUCING DNA IMPURITIES IN VIRAL COMPOSITIONS

FIELD OF THE INVENTION

This invention relates generally relates to the manufacture of vaccines, particularly the purification of viruses and more particularly the purification of viruses by the elimination of residual DNA from the cell substrate used for the propagation of the virus. In particular, the invention relates to the production of viruses using continuous cell lines and more particularly for the use of Vero cells. The production process may involve the harvesting of the target virus particles, clarification of the viral composition, inactivation of the virus and further purification by combining the viral composition with a solution with high ionic strength followed by size exclusion chromatography. The invention is useful for the production of viruses, and in particular rabies viruses, for the manufacture of medical products, such as vaccines for humans and animals.

BACKGROUND OF THE INVENTION

1. Introduction

Modified virus particles are used for multiple human medical applications such as vaccines. In such cases it is imperative that the virus composition used is purified such that potential medical risks, such as adverse side effects due to undesirable impurities, is eliminated, or as a minimum reduced to an acceptable level. Purification processes involve the removal of various impurities including unwanted residual DNA fragments originating from the cell substrate used to culture the virus. However, while the purification process must deliver products that meet the most stringent regulatory safety standards, the purification methods used must not degrade the medicinal properties of the virus itself, nor make the production process uneconomical so that the finished medical product becomes prohibitively expensive.

Purification techniques relying on the use of nuclease or chemicals to degrade the residual DNA into fragments too small to represent a significant clinical risk may result in degrading of the virus particles thereby detrimentally reducing the immunogenicity of the target virus. The various filtration, centrifuge and other techniques to clarifying the viral solution that rely on the differentiated physical properties of the desired virus as compared with the unwanted impurities (such as size weight, density and the like) may not adequately remove the DNA to levels that meet regulatory standards for medical products.

Purification techniques such as ionic chromatography and the like that rely on the differential electronic charges associated with the viral particles and the unwanted impurities may result in low production yields and thus high production costs.

The present invention provides a cost effective means to standardize the bulk production of highly purified viral compositions while retaining the immunogenicity of the virus particles. The present invention therefore meets the need to produce high quality, efficacious and affordable virus compositions that may meet international regulatory standards for safety and efficacy and are thus suitable for human medical applications. For over 45 years viruses for vaccines have been propagated using primary cells from various sources including; chicken embryos as well as monkey, dog, rabbit and hamster kidney cells. While products resulting from these manufacturing process are considered to be safe for human use, potential contamination by infectious pathogens, inconsistencies between individual animals and the ethical sensitivities of collecting animal cells resulted in the search for alternative cell substrates.

Diploid cells were found to overcome many of the shortcomings observed with primary cells. Diploid cells are well tolerated, non-tumorigenic, have a low frequency of chromosomal abnormalities and have a finite capacity for serial propagation. However, diploid cells are difficult to use in bulk quantities and environmental conditions are more stringent for successful use.

Continuous cell lines, a third class of cell substrate, are increasingly becoming the preferred option for virus production. The advantages of continuous cell lines are, the indefinite production of standard and well-characterized cells that grow efficiently and may be used for large-scale virus production in bioreactors. The WHO established a master cell bank for Vero cells, a continuous cell lines derived from the kidneys of African green monkeys being a cell line considered to be advantageous for the production of vaccine antigens (WHO Tech. Rep. 747 1987).

However, continuous cell lines themselves are associated with certain disadvantages relating to their use for medical purposes. Residual DNA may be capable of being integrated into the host genome, which may potentially result in malignant transformations of the host's/recipient's DNA leading to abnormalities in cell replication such as cancer.

Four factors impact the magnitude of the risk; the cell-substrate itself, different types have different safety profiles, the size of the DNA fragment i.e. below 200 base pairs is generally less than the size of a functional gene, the route of administration i.e. the up-take of DNA is approximately 10,000-fold less efficient in orally as opposed to parenterally administered compositions, and the concentration of DNA present.

The FDA's Code of Federal Regulations Title 21 part 610.13 under the general standards for biological products states that "Products shall be free of extraneous material except that which is unavoidable in the manufacturing process described in the approved biologics license application". Specific regulations or guidelines have also been issued by the WHO and national regulatory bodies designed to control the level of DNA content in vaccine antigens derived from production processes using continuous cell lines.

The WHO expert committee on biological standardization technical report 878 issued in 1998 concluded that "The risk associated with residual continuous cell line DNA in a product is negligible when the amount of such DNA is 100 pg or less per parenteral dose." The conclusion of the committee's assessment was that up to 10 ng of residual continuous-cell-line DNA per purified dose of vaccine was considered acceptable.

The European Agency for the Evaluation of Medicinal Products Committee for Proprietary Medicinal Products published a position statement in 2001 on the Use of Tumourigenic Cells of Human Origin for the Production of Biological and Biotechnological Medicinal Products cites the WHO conclusion above but also notes that the WHO report states that instances occur where the potential for clinical risks are higher, for example, where the residual DNA may contain infectious retroviral provirion sequences. The report concludes that the DNA level permitted in the final product "Should be as low as possible" and based on an assessment of the risk factors on a case-by-case basis.

The FDA's Guidance for Industry "Characterization and qualification of cell substrates and other biological materials used in the production of viral vaccines for infectious disease indications" issued in 2010 states that "You should limit residual DNA for continuous non-tumorigenic cells, such as low-passage Vero cells, to less than 10 ng/dose for parenteral inoculation as recommended by WHO." The recommendation for orally administered compositions is less than 100 ug per dose given the naturally lower uptake for this administration method.

The 2010 Chinese Pharmacopeia issued by a committee headed by the Chairman of the Chinese Food and Drug Association (SFDA) states that the residual DNA from Vero cell substrates used in the production process for rabies vaccines must be less than 100 pg per dose i.e. 0.1 ng per dose or 100 fold less than the WHO recommendation (see above).

There is a continual medical need for a reliable large-scale supply of economically produced high quality virus compositions suitable for human medical applications including, but not limited to vaccines. In this context quality is defined as both, i) the antigenic properties of the virus such that it delivers the desired medical outcomes and ii) concurrently the purity of the viral compositions such that any contaminants introduced during the manufacturing process, for example DNA from the cellular substrate, are eliminated or reduced to an acceptable minimal level in the finished product to ensure that the composition is safe for human use.

One objective of the current invention is thus to propose a novel method for purifying viruses in very high yield which is easy to automate.

Another objective of the current invention is to propose a purification method that allows for whole, non-degraded viruses to be obtained.

A further objective of the current invention is to propose a purification method that significantly reduces concentration of unwanted impurities and specifically to reduce significantly the residual DNA from the cell line substrate in the finished product, thereby producing highly purified virus particles.

Yet another objective of the current invention is to propose a purification process that is scalable, i.e. it is possible to produce bulk quantities of the desired purified viral composition.

It is also an object of the present invention to improve the processing technology, simplify the equipment required, minimize the production costs, and ensure batch-to-batch consistency.

To achieve these aims, the subject of the invention is a method for purifying a viral culture, wherein according to the invention the purification of a viral culture is characterized by a method consisting of a combination of processes that includes at least one step to increase the ionic concentration of the viral composition and then at least one step to separate the desirable virus from the unwanted residual DNA by size exclusion chromatography. The result of this process is a composition of purified viruses that may be used to produce highly effective vaccines causing no significant adverse side effects in the recipients.

2. Description of Related Art

Methods for purifying viruses are known in the prior art. One approach to the purification of residual DNA is to degrade the DNA to a size small enough to mitigate the risk of functional residual fragments of DNA, that is, reducing the chances of the residual DNA retaining a functional gene to a clinically acceptable level.

One approach to the degradation of DNA is the introduction of nuclease, the enzyme selected on the basis of it being capable of breaking down the residual DNA fragments. Methods of using nuclease before or after cell lysation as described in the patent applications US 2009/0017523 and US2009/0123989. The degrading of the unwanted DNA may also be achieved by methods other than the introduction of nuclease, for example the use a chemical composition such as those described in patent application US 2009/0304729.

However, degrading the DNA fragments is not the preferable solution because the compositions, nuclease or otherwise, used to degrade the unwanted DNA tend also to have a detrimental effect on the immunogenicity of the target virus. To meet the overall objectives the resulting viral composition must have both a low residual DNA concentration and virus particles with the desired immunogenicity. Furthermore, the nuclease, chemical or other substance used to degrade the DNA must itself be then removed from the viral composition. Thus, in accordance with the current invention, the method of purification is characterized in part by the process of DNA removal or reduction without the use of nuclease.

Detergents may be use to precipitate DNA into a suspension within the viral composition thereby facilitating the removal of the DNA by means of filtration or centrifuge techniques. However, the detergent itself must then be removed from the final virus composition resulting in additional steps and costs in the manufacturing process. Thus, in accordance with the current invention, the method of purification is characterized in part by the process of DNA removal or reduction without the use of a detergent.

Size exclusion chromatography has been used to eliminate unwanted residual DNA from viral compositions, and specifically rabies virus compositions as produced on continuous cell line substrates, such as Vero cell (see Chtioui et. al. 2007, Kumar et. al. 2002 and Kumar et. al. 2005). Size exclusion, as described in the prior art, is conducted at low salt concentrations wherein "Low salt concentration" is exemplified by up to 0.5M NaCl. Such prior art publications fail to teach the benefits of using high ionic concentration buffers prior to the size exclusion chromatography to further enhance the removal of unwanted residual DNA.

Another approach described in the prior art is the use of ionic chromatography. Ionic chromatography has certain limitations in that the resulting yield of purified virus is significantly reduced, as compared with size exclusion chromatography (Purification of rabies virus produced on Vero cells using chromatography techniques, Chtioui et. al. 2007), making such ionic chromatography process unsuitable for large-scale virus production.

The advantage of the current invention is that while a significant reduction of residual DNA is achievable the overall process may be conducted at commercial scale with a high yield of virus suitable for medical use such as the production of vaccines.

3. Reference Information

U.S. 2009/0017523 Virus Purification Methods

U.S. 2009/0123989 Virus Purification Using Ultrafiltration

U.S. 2009/0304729 Cell-derived Viral Vaccines with Low Levels of Residual Cell DNA U.S. Pat. No. 6,194,191 Method for the production and purification of adenoviral vectors Purification of Rabies Virus Produced on Vero Cells Using Chromatography Techniques Chtioui et. al. Cell Technology for Cell Products, 629-634 2007

Process Standardization for Optimal Virus Recovery and Removal of Substrate DNA and Bovine Serum Proteins in Vero Cell-Derived Rabies Vaccine, Kumar et. al. Journal of Bioscience and Bioengineering, Vol. 94, No. 5, 3375-383, 2002

Purification, Potency and Immunogenicity Analysis of Vero Cell Culture-derived Rabies Vaccine: a Comparative Study of Single-step Column Chromatography and Zonal Centrifuge Purification, Microbes and Infection 7 (2005) 1110-1116 Kumar at. al. 2005

Chinese Pharmacopeia 2010

WHO Technical Report Ref. 747 issued in 1987

US FDA's Code of Federal Regulations Title 21 part 610.13

WHO Technical Report Ref 878 issued in 1998

European Agency for the Evaluation of Medicinal Products Committee for Proprietary Medicinal Products: position statement on the Use of Tumourigenic Cells of Human Origin for the Production of Biological and Biotechnological Medicinal Products issued in 2001

FDA's Guidance for Industry "Characterization and qualification of cell substrates and other biological materials used in the production of viral vaccines for infectious disease indications" issued in 2010

DESCRIPTION OF THE INVENTION

The invention relates to the field of purification of viruses, specifically to the purification of viruses obtained by culturing on cell lines and more particularly where continuous cell lines are used as the substrate for virus propagation and even more particularly where the cell substrate comprises Vero cells.

In the subject matter of the present invention the harvested viral composition contains not only the target viruses but also DNA, originating from the culture cells, and other unwanted impurities. When such viruses are produced for medical use, such as the manufacture of vaccines, it is preferable for them to be as pure as possible i.e. the content of residual DNA and other impurities are reduced to a level where there is no risk or a minimal clinically acceptable minimal risk of any adverse side effect. As a minimum the purity of the final virus composition must comply with the appropriate regulatory standard for both safety and efficacy.

The subject matter of the current invention includes all viruses, particularly viruses of the order mononegavirales and more particularly the family of Rhabdoviridae and even more particularly rabies viruses. The subject matter of the current invention also applies in particular to viruses suitable for propagation with continuous cell lines, for example; rabies, poliomyelitis, hemorrhagic fever, Japanese Encephalitis and the like.

In certain embodiments of the present invention the steps used to harvest exclude the use of nuclease or other substances to lysate the cells of the cell substrate. In further embodiments of the current invention no chemicals, such as detergents, are used to precipitate the DNA, which may facilitate the removal of the DNA from solution containing the target virus. In yet further embodiments of the current invention no chemicals are used to degrade the DNA thereby reducing the size of the DNA to mitigate the risk of there being fragments of DNA that retain a functional gene.

The subject matter of the current invention includes all cell substrates suitable for virus propagation, particularly continuous cell lines and more particularly Vero cells. The selected cell line will be cultured and infected with the target virus under suitable environmental conditions.

In certain embodiments of the current invention, after an appropriate period of time under the desired conditions necessary to culture the virus, the viral composition is harvested. In related embodiments of the present invention the undesirable impurities in suspension are substantially removed through a filtration. The use of such techniques generally rely on the different physical properties of the target virus as compared with the unwanted impurities, (such as size), to purify or clarify the viral solution.

Whereas certain residual cell substrate DNA in the virus solution, particularly the precipitated DNA fragments in suspension, may be removed through filtration.

The effect of the binding affinity between the residual DNA and virus particles may be further compounded during the concentration of the virus particles because the DNA may become physically trapped during the aggregation of the virus particles. Once the DNA is bound Specifically or Non-specifically to the virus, or otherwise entrapped by aggregates of the virus, the use of ultrafiltration and/or size exclusion as described in the art becomes relatively ineffective as a means for efficiently removing the DNA.

The present invention further relates to a process for purifying the resulting harvested virus, which will preferably, but not necessarily, includes at least the following steps: clarification of the virus solution, by filtration to remove cell debris and part of unbound residual DNA from the cell substrate, an step to concentrate the purified virus to levels useful for further processing, washing the virus in high and then low salt buffer, an inactivation step whereby the harvested virus is rendered inactive by treatment with chemicals or other process known to those skilled in the art.

The viral solution at this stage of the purification process generally still contains a concentration of residual DNA from the cell substrate in excess of 100 pg per ml, that is, the viral composition would not be anticipated to meet the Chinese FDA guidelines for the maximum concentration of DNA content suitable for human use as set out in the Chinese Pharmacopeia 2010.

The present invention is exemplified by the inclusion of two additional important steps in the purification process, namely the washing of the concentrated virus composition in a high ionic (that is a high salt) solution followed by size-exclusion chromatography resulting in the unexpected removal of significant amounts of residual DNA, thus providing a more robust and economically feasible method for preparing large, commercial grade quantities of highly purified viruses.

In certain embodiments of the current invention, following suitable processing of the virus in a high ionic strength buffer followed by size exclusion chromatography the DNA concentration of the virus composition may be less than 100 pg per ml, preferably between 10 and 100 pg per ml and more preferably between 10 and 50 pg per ml. Such viral compositions would be anticipated to meet the SFDA standards for residual DNA content as described in the Chinese Pharmacopeia 2010.

In certain embodiments of the present invention an additional filtration step is performed post the size-exclusion chromatography to remove additional particulates prior to using the virus for medical purposes. The viral composition may be subsequently diluted or otherwise adjusted to suit the formulation requirements of the specific target medical products.

The overall result of the current invention overcomes the limitations of the prior art by providing a standard process for the purification of viral compositions that involves the removal of impurities and particularly the removal of cellular DNA to the maximum possible extent, while retaining the desired antigenic properties of the target virus, that may be then used for products suitable for human medical use.

The invention will be better understood on reading the detailed description that follows.

DESCRIPTION OF THE FIGURES

No drawings.

DETAILED DESCRIPTION OF EXEMPLARY EMBODIMENTS OF THE INVENTION

The present invention may be understood more readily by reference to the following detailed description of certain embodiments of the invention and the Examples included herein.

Throughout this application, where publications are referenced, the disclosures of these publications are hereby incorporated by reference, in their entireties, into this application in order to more fully describe the state of art to which this invention pertains.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "a text" includes a plurality of such texts and reference to "the segment" includes reference to one or more segments and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Definitions of Terms

"Specific" binding or "Specifically" bound herein refers to DNA fragments that have become isolated from the cell substrate and fused with the DNA of the target virus or otherwise bound at a particular location of the virus, on the surface or otherwise, that has enhanced or particular binding affinity to the structure of the DNA fragment.

"Non-specific" binding or "Non-specifically" bound DNA herein refers to DNA that is in some way bound to the virus through electronic or physical affinity but not genetically integrated with the viral genome nor associated with any particular site of the virus.

Certain units of measure have been used throughout the document following the standard conventions for abbreviation such as; "ug" for micro-grams "pg" for pico-grams, "ng" for nano-grams, "ml" for milli-liters and "l" for liters.

Overview of the Invention

The present invention relates to the purification of viral compositions preferably under sterile conditions, in particular the removal of impurities and more particularly the removal of residual DNA from the cell substrate used in the propagation of the virus. By removal of such impurities the resulting virus composition may be suitable for use in medical applications, for example the production of vaccines for human or animal use, without exposing the vaccine's recipient to undue risk associated undesirable adverse side effects associated with any impurities in particular impurities arising the presence of residual DNA fragments from the host cell culture used in the propagation of the target virus.

The subject matter of the present invention relates to a process for the purification of viral compositions that results in the cost effective recovery of commercially viable quantities of immunogenic virus particles with excellent purity characteristics, making this methodology especially useful for the preparation of medicinal products for human use such as vaccines.

One embodiment of the present invention describes a method of purifying virus particles. In particular, the present invention relates to methods of purifying virus particles that comprises removing all or some of the residual DNA impurities, such as DNA fragments from host cells used to propagate the target virus, from the virus particles by a multi-step process characterized by immersing the virus particles in a buffer with a high ionic concentration followed by a chromatography step to remove the DNA impurities.

A related embodiment of the present invention describes a method of purifying virus particles. In particular, the present invention relates to methods of purifying virus particles that comprises removing all or some of the residual DNA impurities, such as DNA fragments from host cells used to propagate the target virus, from the virus particles by a multi-step process characterized by immersing the virus particles in a buffer with a high ionic concentration followed by a size exclusion chromatography step to remove the DNA impurities.

In a still further related embodiment of the present invention describes a method of purifying virus particles. In particular, the present invention relates to methods of purifying virus particles that comprises removing all or some of the residual DNA impurities, such as DNA fragments from host cells used to propagate the target virus, from the virus particles by a multi-step process characterized by immersing the virus particles in a buffer with a high ionic concentration followed by inactivation of the target virus followed by size exclusion chromatography step to remove the DNA impurities.

In an additional related embodiment of the present invention describes a method of purifying virus particles. In particular, the present invention relates to methods of purifying virus particles that comprises removing all or some of the residual DNA impurities, such as DNA fragments from host cells used to propagate the target virus, from the virus particles by a multi-step process characterized by immersing the virus particles in a buffer with a high ionic concentration followed by inactivation of the target virus followed by size exclusion chromatography step to remove the DNA impurities wherein the DNA fragments are Specifically and/or Non-specifically bound to the target virus.

The ionic strength of buffer solution may be determined from both molar concentration and charge numbers of all the ions present in the solution. The ionic strength, I, may be calculated using following formula:

$$I = \frac{1}{2}\sum_{i=1}^{n} c_i z_i^2$$

where $c_i$ is the molar concentration of ion i (mol·dm$^{-3}$), $z_i$ is the charge number of that ion, and the sum is taken over all ions in the solution. Generally a 1:1 electrolyte such as NaCl, the ionic strength is equal to its molar concentration, while multivalent ions contribute more to the ionic strength in the solution, for example, the ionic strength of the 2:2 electrolyte MgSO$_4$ is four times that of NaCl.

In certain embodiment of the present invention, the ionic strength of the buffer which is used to wash the virus particles before size exclusion chromatography is preferably between 0.5 to 5.0 mol/L, more preferably between 0.8 to 2.0 mol/L and most preferably between 0.8 to 1.2 mol/L.

In certain embodiments of the invention the virus will be selected from one of the following viral classifications; dsDNA viruses, ssDNA viruses, dsRNA viruses, (+)ssRNA viruses, (−)ssRNA viruses, ssRNA-RT viruses or dsDNA-RT viruses.

In certain embodiments of the invention the virus will be selected from the order mononegavirales, or preferably the rhabdoviridae family, or more preferably the lyssavirus genus or even more preferably the rabies species of virus either a wild type or modified rabies virus, or more preferably certain types of rabies virus strains including, but not limited to, PM rabies virus, PV rabies virus and as an exemplary rabies virus further discussed herein the CTN rabies virus.

In related embodiments of the current invention the virus may be an envelope virus or a retro virus.

The subject matter of the current invention also applies in particular to viruses suitable for propagation with continuous cell lines, for example; rabies, poliomyelitis, hemorrhagic fever, Japanese Encephalitis and the like.

The selected virus is first propagated in a host cell line wherein the cell line may be derived from a primary cell lines, a diploid cell line, a heteroploid cell line or a continuous-cell-line.

In certain embodiments of the invention the preferred cell line would be a continuous cell line. The continuous cell line may be selected from, but not limited to, one of the following cell lines; PER.C6, NIH-3T3, BHK, CHO, Vero and MDCK.

Techniques for the selection of an appropriate cell line for the propagation of a particular virus are well known to one skilled in the art It is preferable that the cell line be a continuous cell line and more preferable that the source of the cultured cells originate from a mammal, most likely from a primate and especially a non-human primate. An exemplary cell line that may be used for the propagation of the CTN rabies virus is the Vero cell.

Any upstream virus production process known in the art, which can be adapted to large scale cell culture of preferably continuous cell lines and more preferably Vero cells, may be used to generate a virus infected host cell culture. The cell culture is to be subjected to a post-infection period of culture for virus replication under conditions known to one skilled in the art so as to maximize the amount of intracellular and/or extracellular virus) for the purification methodology of the present invention. Methods of cell culture are known in the art, for example, U.S. Pat. No. 6,194,191 incorporated herein in its entirety, provides a review of cell culture techniques that may be adapted from virus to virus and cell culture to cell culture to optimize virus yield.

After an appropriate time for culturing the virus-infected cells and replication of the virus, the virus is harvested by techniques known to those skilled in the art. In certain embodiments the virus is collected after lysating the cells in the cell culture with a chemical, nuclease or other equivalent agent. In other embodiments the virus is collected purely from the cell culture supernatant, the cells of the cell culture would only be lysated naturally during the virus replication process. In related embodiments the virus may be harvested from the cell culture supernatant once, or twice, or three or four, or five or more than five times.

In certain embodiments of the present invention the steps used to harvest the virus exclude the use of nuclease or other substances to lysate the cells of the cell substrate. In further embodiments of the current invention no chemicals, such as detergents, are used to precipitate the DNA that may facilitate the removal of the DNA from solution containing the target virus. In yet further embodiments of the current invention no chemicals are used to degrade the DNA thereby reducing the size of the DNA to mitigate the risk of there being fragments of DNA that retain a functional gene.

The resulting live virus is retained in a suitable buffer. In addition to the harvested virus, the buffer solution contains certain unwanted reside resulting from the manufacturing process. In general the unwanted residue consists of cell debris and in particular residual DNA that is, fragments of nucleic acid from the cell substrate.

After harvesting, the buffer solution containing the virus may undergo clarification, that is, one or more process steps to remove cell debris and/or nucleic acid in the buffer. This clarification process provides an effective and economically means remove cell debris suspended in the buffer solution. Any such clarification approach including filtration, microfiltration, or chromatography and the like, which provides a filtrate of suitable clarity will be acceptable to practice within the present invention.

One embodiment of the current invention involves the filtration of the buffer containing the virus particles to remove impurities particularly those in suspension or precipitated in the buffer solution. Techniques for filtration of virus particles are well known to one skilled in the art. The choice of filtration process will be a function in part of the precipitate size distribution relative to the size of the virus particles to be retained. The preferred filtration option will optimize the balance between removing the unwanted residual particles while maintaining a high viral yield that retains the antigenicity of the virus in a cost effective manner. Suitable filters may utilize cellulose filters, regenerated cellulose fibers, cellulose fibers combined with inorganic filter aids, cellulose fibers combined with inorganic filter aids and organic resins, or any combination thereof, and polymeric filters or the like. In general, a multiple stage process is preferable but not required. An exemplary process would be the two stage filtration of the viral solution using first a suitable filter with a pore size not less than 1.5 microns, or not less than 2.0 microns, or not less than 2.5 microns, or not less than 3.0 microns, or not less than 3.5 microns, or not less than 4.0 microns or not less than 4.5 microns or not less than 5.0 microns followed by filtration through a suitable finer filter with a pore size less than 0.5 microns, or less than 1.0 microns or less than 1.5 microns.

In certain embodiments of the current invention the viral content of the supernatant may then be concentrated by any one of a number of processes known to those skilled in the art, for example ultrafiltration or diafiltration and the like.

In one embodiment of the present invention the viral content may be concentrated by ultrafiltration. An exemplary process would be ultrafiltration using a filter medium with a pore size up to 100 kilo Daltons, or up to 200 kilo Daltons, or up to 300 kilo Daltons, or up to 400 kilo Daltons or up to 500 kilo Daltons to produce a viral solution with a concentration of greater than 10 times, or greater than 20 times, or greater than 30 times, or greater than 40 times, or greater than 50 times, or greater than 60 times, or greater than 70 times, or greater than 80 times, or greater than 90 times, or greater than 100 times, or greater than 110 times, or greater than 120 times the original supernatant.

In certain embodiments of the current invention the resulting viral supernatant is then washed. Techniques for washing viral solutions are known by one skilled in the art. An exemplary process would be to wash the viral supernatant once or twice, or three times or four times or five times or six times or seven times, or eight times or nine times, or ten times, or eleven times, or twelve times, or thirteen times, or fourteen times, or fifteen times with an equal volume, double the volume, triple the volume, quadruple the volume, five times six times the volume or seven times the volume, or eight times the volume or nine times the volume, or ten times the volume, or eleven times the volume, or twelve times the volume, or thirteen times the volume, or fourteen times the volume, or fifteen times the volume of PBS with a pH of up to 5, or up to 6, or up to 7, or up to 7.1, or up to 7.2 or up to 7.3, or up to 7.4, or up to 7.5, or up to 7.6, or up to 7.7, or up to 7.8, or up to 7.9, or up to 8 or up to 9 with a solution of high ionic strength achieved using salt concentration of up to 0.5M, or up to 0.6M, or up to 0.7M, or up to 0.8M, or up to 0.9M, or up to 1M, or up to 1.1M, or up to 1.2M, or up to 1.3M, or up to 1.4M, or up to 1.5M, or up to 1.6M, or up to 1.7M, or up to 1.8M, or up to 1.9M, or up to 2M, or up to 2.5M, or up to 3M, or up to 3.5M, or up to 4M, or up to 4.5M or up to 5M wherein the salt solution may comprise any combination of the common cations, eg. Na+, K+, Al3+, Ca2+, Mg2+, NH4+, and common anions, eg. Cl—, (OH)—, (CO3)2-, (504)2-, (PO4)3-, (HCO3)-, (HSO4)-, (HPO4)2-, (H2PO4)-, more specifically comprise Na2SO4, (NH4)2SO4, Na2HPO4, NaCl or KCl, and most specifically comprise NaCl.

In related embodiments of the current invention the viral solution is then washed further in a low salt buffer. An exemplary process would be to wash the viral supernatant once or twice, or three times or four times or five times or six times or seven times, or eight times or nine times, or ten times, or eleven times, or twelve times, or thirteen times, or fourteen times, or fifteen times with an equal volume, double the volume, triple the volume, quadruple the volume, five times six times the volume or seven times the volume, or eight times the volume or nine times the volume, or ten times the volume, or eleven times the volume, or twelve times the volume, or thirteen times the volume, or fourteen times the volume, or fifteen times the volume of PBS with a pH of up to 5, or up to 6, or up to 7, or up to 7.1, or up to 7.2 or up to 7.3, or up to 7.4, or up to 7.5, or up to 7.6, or up to 7.7, or up to 7.8, or up to 7.9, or up to 8 or up to 9 with a salt concentration of up to 0.1M, or up to 0.2M, or up to 0.3M, or up to 0.4M, or up to 0.5M, or up to 0.6M, or up to 0.7M, or up to 0.8M, or up to 0.9M, or up to 1M wherein the salt solution may comprise any combination of the common cations, eg. Na+, K+, Al3+, Ca2+, Mg2+, NH4+, and common anions, eg. Cl—, (OH)—, (CO3)2-, (SO4)2-, (PO4)3-, (HCO3)-, (HSO4)-, (HPO4)2-, (H2PO4)-, more specifically comprise Na2SO4, (NH4)2504, Na2HPO4, NaCl or KCl, and most specifically comprise NaCl.

In further related embodiments of the present invention the target virus may be combined with the high ionic concentration solution prior to the ultrafiltration process as described above. In such embodiments of the present invention the virus may be washed or otherwise purified in the presence of a high ionic solution wherein the solution of high ionic strength is achieved using salt concentration of up to 0.5M, or up to 0.6M, or up to 0.7M, or up to 0.8M, or up to 0.9M, or up to 1M, or up to 1.1M, or up to 1.2M, or up to 1.3M, or up to 1.4M, or up to 1.5M, or up to 1.6M, or up to 1.7M, or up to 1.8M, or up to 1.9M, or up to 2M, or up to 2.5M, or up to 3M, or up to 3.5M, or up to 4M, or up to 4.5M or up to 5M wherein the salt solution may comprise any combination of the common cations, eg. Na+, K+, Al3+, Ca2+, Mg2+, NH4+, and common anions, eg. Cl—, (OH)—, (CO3)2-, (SO4)2-, (PO4)3-, (HCO3)-, (HSO4)-, (HPO4)2-, (H2PO4)-, more specifically comprise Na2SO4, (NH4)2504, Na2HPO4, NaCl or KCl, and most specifically comprise NaCl.

In certain embodiments of the current invention the live virus is then inactivated. Techniques for the inactivation of live viruses are known by one skilled in the art. An exemplary process step would be the treatment of the viral composition with β-propiolactone in a concentration from 0.1% to 0.01% for a period of up to 24 hours at under chilled conditions between 4 and 8 degrees C. followed by a period of up to 2 hours above room temperature between 25 and 40 degrees C. The inactivated virus is then ready for further purification.

In certain embodiments of the current invention the resulting inactivated viral solution is then washed. Techniques for washing viral solutions are known by one skilled in the art. An exemplary process would be to wash the viral supernatant once or twice, or three times or four times or five times or six times or seven times, or eight times or nine times, or ten times, or eleven times, or twelve times, or thirteen times, or fourteen times, or fifteen times with an equal volume, double the volume, triple the volume, quadruple the volume, five times six times the volume or seven times the volume, or eight times the volume or nine times the volume, or ten times the volume, or eleven times the volume, or twelve times the volume, or thirteen times the volume, or fourteen times the volume, or fifteen times the volume of PBS with a pH of up to 5, or up to 6, or up to 7, or up to 7.1, or up to 7.2 or up to 7.3, or up to 7.4, or up to 7.5, or up to 7.6, or up to 7.7, or up to 7.8, or up to 7.9, or up to 8 or up to 9 with a solution of high ionic strength achieved using a salt concentration of up to 0.5M, or up to 0.6M, or up to 0.7M, or up to 0.8M, or up to 0.9M, or up to 1M, or up to 1.1M, or up to 1.2M, or up to 1.3M, or up to 1.4M, or up to 1.5M, or up to 1.6M, or up to 1.7M, or up to 1.8M, or up to 1.9M, or up to 2M, or up to 2.5M, or up to 3M, or up to 3.5M, or up to 4M, or up to 4.5M or up to 5M wherein the salt solution may comprise any combination of the common cations, eg. Na+, K+, Al3+, Ca2+, Mg2+, NH4+, and common anions, eg. Cl—, (OH)—, (CO3)2-, (SO4)2-, (PO4)3-, (HCO3)-, (HSO4)-, (HPO4)2-, (H2PO4)-, more specifically comprise Na2SO4, (NH4)2SO4, Na2HPO4, NaCl or KCl, and most specifically comprise NaCl.

In certain embodiments of the present invention the viral solution is further purified using a chromatographic process. Techniques for chromatography are well known to those skilled in the art.

In a particular embodiment of the current invention the viral solution resulting from the virus inactivation process is further purified by means of size-exclusion chromatography.

In size exclusion chromatography molecules are separated according to size in a bed packed with an inert porous medium, especially an inert gel medium, which is preferably a composite of cross-linked polysaccharides, e.g., cross-linked agarose and dextran in the form of spherical beads. Molecules larger than the largest pores in the swollen gel beads do not enter the gel beads and therefore move through the chromatographic bed fastest. Smaller molecules, which enter the gel beads to varying extent depending on their size and shape, are retarded in their passage through the bed. Molecules are thus generally eluted in the order of decreasing molecular size. Viruses, because of their large size, generally elute in the void volume whereas the unwanted impurities, including but not limited to the residual DNA fragments from the cell substrate, are smaller and are generally trapped within the pores of the inert medium.

The convective fluid flow properties are determined by the bead size. Smaller beads require higher pressure to attain equivalent flow in a column. However, the equilibrium adsorbing capacity is not determined by the bead size. Therefore, the static capacity and the flow properties of the materials are not necessarily coupled or interdependent. However, because most of the capacity is accessed through diffusion, the dynamic binding capacity (capacity in a flow-through mode at a given flow rate) is coupled to the bead size and therefore to the convective flow properties of the adsorbent.

As the beads are porous and the selected molecule to be captured must diffuse into the pores of the media to be captured, the speed and capacity of the system are diffusionally limited. There are two diffusional limitations, one surrounding the bead where a film of material may form and inhibit movement of the selected molecule to the surface of the bead and a second internal diffusional resistance which is determined by the size, number and length of the pores formed in the bead surface. Additionally, the permeability of the media is related to bead size (which can vary widely) as well as the media stability. Larger beads and beads with larger pores tend to have higher permeability. Beads that are not subject to or less subject to compression (by the weight of the beads above them coupled with the pressure under which the fluid flows through the bed) also tend to have greater permeability. However, at high flow rates, permeability does decrease and dynamic capacity also decreases.

It is preferred that the substrate selected be highly porous, so that there is minimal, but sufficient wall or solid material within it to provide the structural integrity and high porosity and flow. The bead sizes may vary from about 100 to about 300 microns, or from about 50 to 150 microns, or from about 20 to about 80 microns or from about 10 to 40 microns, depending upon the fluid and the constituent that is desired to be captured from it. For example, in an application to capture a desired DNA from a composition of virus particles in a buffer solution, the pores of the substrate should be sufficiently large enough to allow good permeability at high flow rates of the broth through the media. The buffer solution use for the chromatography would comprise a standard PBS solution with a pH between about 5 and 9, preferably a pH between about 6 and 8 and more preferably between about 7 and 8.

One embodiment of the present invention further relates to incorporation of an additional downstream clarification process that includes one or more of the following steps in any reasonable combination; filtration, ultrafiltration or chromatography to as a final opportunity to remove any remaining impurities. An exemplary process would be the filtration of the viral solution using a filter with pore size less than 0.25 microns, or less than 0.50 microns, or less than 0.75 microns, or less than 1.0 microns.

The processes of the present invention are scalable from lab-bench scale cell cultures up to commercial scale manufacturing. The present invention thus relates to methodology for the purification of large-scale production of commercially viable amounts of highly purified virus. Where the term "large scale" used herein is considered to be total host cell culture volumes of greater than about 100 liters up to about 2,000 liters, with preferred batch quantities from about 100 liters to about 800 liters.

Techniques to measure the residual DNA in the final solution are well known to those skilled in the art. The preferred technique used is the Dot-blot Hybridization Test as specified in the Chinese Pharmacopeia 2010. Methods to test the antigen content and immunogenicity of viral particles are also well known to those skilled in the art. The preferred tests to measure antigen content and immunogenicity/potency are ELISA and NIH method (animal in vivo testing) respectively, both are to be found in the Chinese Pharmacopeia 2010.

It will be evident to the artisan that the measure of the residual host cell DNA content is not meant as a limitation or defining feature of this methodology. Instead, these data in the examples support the essence of the present invention: a large-scale methodology for the generation of virus particles that results in a highly purified product that may be utilized in clinical and commercial settings. It can be noted that the importance of achieving particular DNA levels in the final product is product-specific. Viral products produced using continuous cell lines for parenteral use in humans will require the most stringent purity standards but, even in that case, the goals may vary from 100 pg per dose up to 10 ng per dose (WHO Requirements for the Use of Animal Cells as in vitro Substrates for the Production of Biologicals Requirements for Biological Substances No. 50), WHO Technical Report Series, No. 878, 1998) or higher, and are likely to be adjusted depending on the product's indication.

In addition, for virus-based products such as vaccines, dosing may vary over several orders-of-magnitude. Therefore, there is no specific significance of achieving a specific residual DNA levels below and, in most applications, variations around that level from lot-to-lot are not likely to be consequential.

Therefore, as noted above, it is preferred that the rabies preparations of the present invention have an immunogenicity of greater than 2.5 IU/dose and preferably greater than 3.5 IU/dose, while having a residual host cell DNA level at least less than 10 ng per dose, or preferably less than 100 pg per dose.

The above disclosure generally describes the present invention. The present invention will be better understood by referring to the following examples of embodying the process for the purification of viruses. These examples are described solely for the purposes of illustrating and are not intended to limit the scope of the invention. Changes in form and substitution of equivalents are contemplated as circumstances may suggest or render expedient. Although specific terms have been employed herein, such terms are intended in a descriptive sense and not for the purposes of limitation.

EXAMPLE

Determination of the Residual DNA Content Before and after Purification

Example 1

Old Process without High Ionic Concentration Buffer

This example illustrates how the residual DNA content of a rabies virus solution is not reduced when the purification process does not include washing the virus composition with a high ionic concentration buffer.

The CTN rabies virus was cultured in Vero cells with the live rabies virus harvested from the supernatant i.e. without use of a nuclease. The viral supernatant was first clarified to remove residual DNA in suspension, and then the live rabies virus particles were then concentrated up to 50 times the original concentration by ultrafiltration, washed in a low salt concentration buffer before being chemically inactivated with β-propiolactone. The antigen content and residual DNA were measured at this point using standard tests as defined in the Chinese Pharmacopeia 2010 (see table 1 below). The viral solution was then subject to size exclusion chromatography using 4FF Sepharose medium. The antigen content and residual DNA were measured at this point using standard tests as defined in the Chinese Pharmacopeia 2010 (see table 1 below).

The viral composition was then filtered before a final assessment of the antigen content and residual DNA were measured at this point using standard tests as defined in the Chinese Pharmacopeia 2010 (see table 1 below).

The above procedure was repeated three times with different batches of the rabies virus.

TABLE 1

Antigen and DNA Content of Rabies Virus

| Process Stage | Batch | Antigen IU/ml | DNA pg/ml |
|---|---|---|---|
| After concentration washing in high salt and low salt buffers and inactivation of the live rabies virus | 1 | 14.8 | 500-1,000 |
|  | 2 | 18.5 | 100-500 |
|  | 3 | 18.0 | 1,000-10,000 |
| After size exclusion chromatography | 1 | 13.6 | 500-1,000 |
|  | 2 | 14.5 | 100-500 |
|  | 3 | 14.3 | 1,000-10,000 |

TABLE 1-continued

Antigen and DNA Content of Rabies Virus

| Process Stage | Batch | Antigen IU/ml | DNA pg/ml |
|---|---|---|---|
| After final filtration | 1 | 13.4 | 500-1,000 |
|  | 2 | 14.5 | 100-500 |
|  | 3 | 14.1 | 1,000-10,000 |

Conclusion: there was no observable reduction in the DNA content of the original virus supernatant as a result of the above purification process.

Example 2

Effect of Ionic Concentration on DNA Removal in Lab Scale

This example illustrates the effect of different ionic concentration on reduction of residual DNA content of a rabies virus solution in lab scale The CTN rabies virus was cultured in Vero cells with the live rabies virus harvested from the supernatant i.e. without use of a nuclease. The viral supernatant was filtered and then concentrated up to 50 times the original concentration by ultrafiltration washed first in a high ionic concentration buffer followed by washing in a low salt concentration buffer before being chemically inactivated with β-propiolactone. The antigen content and residual DNA were measured at this point using standard tests as defined in the Chinese Pharmacopeia 2010 (see table 2 below).

The viral solution was then washed with a with a high ionic concentration buffer containing 0.5M(B), 1M(C), 2.0M(D), 3.0M(E) NaCl and regular PBS buffer (A). After washing the viral solution was then subject to size exclusion chromatography using 4FF Sepharose medium. The antigen content and residual DNA were measured at this point using standard tests as defined in the Chinese Pharmacopeia 2010 (see table 2 below).

The above procedure was repeated three times with different batches of the rabies virus.

TABLE 2

Antigen and DNA Content of Rabies Virus

| Process Stage | Treatment | DNA pg/ml Batch | | | Antigen IU/ml Batch | | |
|---|---|---|---|---|---|---|---|
| After concentration washing in high salt and low salt buffers and inactivation of the live rabies virus | A | 500 pg-1 ng | 500 pg-1 ng | 300-500 pg | 17.4 | 16.7 | 15.2 |
|  | B | 500 pg-1 ng | 500 pg | 300-500 pg | 17.0 | 16.5. | 15.5 |
|  | C | 200-300 pg | 200-300 pg | 200-300 pg | 16.8 | 16.1 | 15.1 |
|  | D | 100-200 pg | 100-200 pg | 100-200 pg | 16.9 | 15.4 | 14.4 |
|  | E | 50-100 pg | 50-100 pg | 50-100 pg | 12.9 | 11.4 | 10.4 |
| After size exclusion chromatography | A | 300 pg | 200-300 pg | 300-500 pg | 15.1 | 14.1 | 13.4 |
|  | B | 200-300 pg | 200 pg | 100-150 pg | 15.5 | 14.4 | 13.6 |
|  | C | 10-50 pg | 10-50 pg | 10-50 pg | 14.2 | 14.2 | 12.5 |
|  | D | 10-50 pg | 10-50 pg | 10-50 pg | 13.3 | 13.2 | 11.1 |
|  | E | 10-50 pg | 10-50 pg | 10-50 pg | 10.3 | 10.1 | 9.8 |

IU-International Units
A: regular PBS;
B: PBS with 0.5 M Nacl;
C: PBS with 1.0 M Nacl;
D: PBS with 2.0 M Nacl;
E: PBS with 3.0 M Nacl
Conclusion: the combined processes of washing the viral supernatant in a high ionic concentration buffer followed by size exclusion chromatography dramatically reduced the concentration of unwanted residual DNA in lab scale. It should be noted that along with the increasing of ioinc centration, the DNA reduced dramatically, but the antigen recovery also dicreased.

Example 3

New Process with High Ionic Concentration Buffer in Large Scale

This example illustrates how the residual DNA content of a rabies virus solution may be reduced while retaining the immunogenicity of the rabies virus particles.

The CTN rabies virus was cultured in Vero cells with the live rabies virus harvested from the supernatant i.e. without use of a nuclease. The viral supernatant was filtered and then concentrated up to 50 times the original concentration by ultrafiltration, washed first in a high ionic concentration buffer followed by washing in a low salt concentration buffer before being chemically inactivated with β-propiolactone. The antigen content and residual DNA were measured at this point using standard tests as defined in the Chinese Pharmacopeia 2010 (see table 3 below).

The viral solution was then washed with a high ionic concentration buffer containing 1M NaCl. After washing the viral solution was then subject to size exclusion chromatography using 4FF Sepharose medium. The antigen content and residual DNA were measured at this point using standard tests as defined in the Chinese Pharmacopeia 2010 (see table 3 below).

The viral composition was then filtered before a final assessment of the antigen content and residual DNA were measured at this point using standard tests as defined in the Chinese Pharmacopeia 2010 (see table 3 below).

The above procedure was repeated three times with different batches of the rabies virus.

TABLE 3

Antigen and DNA Content of Rabies Virus

| Process Stage | Batch | Antigen IU/ml | DNA pg/ml |
|---|---|---|---|
| After concentration washing in high salt and low salt buffers and inactivation of the live rabies virus | 1 | 19.6 | 500-1,000 |
| | 2 | 17.0 | 300-500 |
| | 3 | 20.6 | 300-400 |
| After size exclusion chromatography | 1 | 15.7 | 10-50 |
| | 2 | 16.7 | 50-100 |
| | 3 | 13.7 | 10-50 |
| After final filtration | 1 | 15.7 | 10-50 |
| | 2 | 16.9 | 50-100 |
| | 3 | 14.5 | 10-50 |

IU—International Units

A rabies virus composition with an antigen content of 13 IU/ml will be expected to have an immunogenic potency in excess of 6 IU/ml. Hence for all three of the above samples a vaccine dose of 0.6 ml or 1.0 ml per dose will have an immunogenic potency greater than the WHO/Chinese Pharmacopeia standard of 2.5 IU/dose, deemed to be the minimum required potency needed for human use.

Conclusion: the combined processes of washing the viral supernatant in a high ionic concentration buffer followed by size exclusion chromatography dramatically reduced the concentration of unwanted residual DNA while not adversely affecting the immunogenicity of the inactivated rabies virus particles.

What is claimed is:

1. A method for the removal of DNA impurities from viral compositions, the method comprising the steps of: a) harvesting the virus from the cell culture supernatant without the use of a nuclease, followed by b) combining the virus with solution that has an ionic strength of between 0.5 mol/L and 3.0 mol/L followed by c) size exclusion chromatography.

2. The method according to claim 1, wherein the virus belongs to the order mononegavirales.

3. The method according to claim 1, wherein the virus is a rabies virus.

4. The method according to claim 1, wherein the virus is an envelope virus.

5. The method according to claim 1, wherein the virus is a rabies virus and the cell culture is a continuous cell line.

6. The method according to claim 1, wherein the virus is a rabies virus and the cell culture is a Vero cell.

7. The method according to claim 1, wherein the virus is a rabies virus and the cell culture is a Vero cell and the harvested rabies virus is deactivated using between 0.1% and 0.01% β-propiolactone.

* * * * *